United States Patent
Hooper et al.

(10) Patent No.: US 8,436,995 B2
(45) Date of Patent: May 7, 2013

(54) METHOD OF OPTIMISING THE SENSITIVITY OF A SURFACE PLASMON ELLIPSOMETRY APPARATUS

(75) Inventors: Ian Richard Hooper, Devon (GB); John Roy Sambles, Devon (GB); Ciaran Eoin Stewart, Devon (GB)

(73) Assignee: Attomarker Limited (GB)

( * ) Notice: Subject to any disclaimer, the term of this patent is extended or adjusted under 35 U.S.C. 154(b) by 308 days.

(21) Appl. No.: 12/740,095

(22) PCT Filed: Oct. 27, 2008

(86) PCT No.: PCT/GB2008/051001
§ 371 (c)(1),
(2), (4) Date: Jun. 17, 2010

(87) PCT Pub. No.: WO2009/056875
PCT Pub. Date: May 7, 2009

(65) Prior Publication Data
US 2010/0259754 A1    Oct. 14, 2010

(30) Foreign Application Priority Data
Nov. 1, 2007 (GB) .................................. 0721482.8

(51) Int. Cl.
G01J 4/00    (2006.01)
(52) U.S. Cl.
USPC ........................................................ 356/369
(58) Field of Classification Search ............... None
See application file for complete search history.

(56) References Cited

U.S. PATENT DOCUMENTS

| 7,233,396 B1 * | 6/2007 | Hall et al. .................... 356/369 |
| 7,586,614 B2 * | 9/2009 | VanWiggeren et al. ...... 356/445 |
| 2004/0142482 A1 | 7/2004 | Westphal et al. |

OTHER PUBLICATIONS

International Preliminary Report on Patentability dated May 4, 2010 from corresponding International Application No. PCt/GB08/051001.
Stewart, C.E., et al., "Surface plasmon differential ellipsometry of aqueous solutions for bio-chemical sensing" Journal of Physics D. Applied Physics, IOP Publishing, Bristol, GB, vol. 41, No. 10, May 21, 2008.
Chao, et al., "Post flight analysis of the surface plasmon resonance enhanced photoelastic modulated ellipsometry," Sensors and Actuators B, Elsevier Sequoia S.A., Lausanne, CH, vol. 121, No. 2, Feb. 3, 2007, pp. 490-495.
Hooper, I., et al., "Sensing using differential surface plasmon ellipsometry," Journal of Applied Physics, American Institute of Physics, New York, US, vol. 96, No. 5, Jan. 1, 2004, pp. 3004-3011.
The ISR and Written Opinion from corresponding International Application No. PCT/GB08/051001 dated Jan. 26, 2009.

* cited by examiner

Primary Examiner — Tu Nguyen
(74) Attorney, Agent, or Firm — Snell & Wilmer L.L.P.

(57) ABSTRACT

A method of optimising the sensitivity of surface plasmon ellipsometry (SPE) apparatus used to analyse a surface comprising a conducting film is disclosed. The method includes calculating a sensitivity map of plasmon ellipsometry for the film. The sensitivity map comprises data defining variations in sensitivity of the plasmon ellipsometry apparatus with angle of incidence and polarization angle of polarized light incident on the conducting film for analysis by the apparatus. The method further comprises using the sensitivity map to configure the plasmon ellipsometry apparatus with a combination of the angle of incidence and polarization angle located in a region of substantially maximum sensitivity in the sensitivity map.

12 Claims, 4 Drawing Sheets

METHOD OF OPTIMISING THE SENSITIVITY OF A SURFACE PLASMON ELLIPSOMETRY APPARATUS

CROSS-REFERENCE TO RELATED APPLICATIONS

This application is U.S. national phase filing under 35 U.S.C. §371 of PCT/GB2008/051001 filed Oct. 27, 2008 and claims priority from United Kingdom Application No. GB 0721482.8 which was filed on Nov. 1, 2007.

This invention relates to a plasmon resonance based sensor and to methods and apparatus for reading such sensors.

BACKGROUND

The interest in optical biological and chemical sensing technologies has never been higher than in recent years. The demand for increased sensitivity and parallelism has arisen not only from areas of pure research, such as the burgeoning field of proteomics, but also from the pharmaceutical industries due to its utilisation in drug discovery processes. A wide range of optical methods are exploited in bio-chemical sensors including interferometry (e.g. Cush R, Cronin J M, Stewart W J, Maule C H and Mollow J 1993 The resonant mirror: a novel optical biosensor for direct sensing of biomolecular interactions Part I: Principle of operation and associated instrumentation *Biosens. Bioelec.* 8 347-354), spectroscopy in optical waveguides (e.g. Heideman R G, Kooyman R P H and Greve J 1993 Performance of a highly sensitive optical waveguide Mach-Zehnder interferometer immunosensor *Sens. Actuators B.* 10 209-217), fluorescence spectroscopy (e.g. Rowe-Taitt C A, Hazzard J W, Hoffman K E, Cras J 5, Golden J P and Ligler F S 2000 Simultaneous detection of six biohazardous agents using planar waveguide array biosensor *Biosens. Bioelec.* 15 579-589) and surface plasmon resonance (SPR) (e.g. Homola J 2003 Present and future of surface plasmon resonance biosensors *Anal. Bioanal. chem.* 377 528-539 or Nylander C, Liedberg B and Lind T 1982 Gas detection by means of surface plasmon resonance *Sens. Actuators.* 3 79 (1982)). Fluorescence spectroscopy offers ultra-high sensitivity but requires the use of fluorescent labels, which is frequently undesirable. On the other hand interferometric, waveguiding and SPR techniques have the advantage of being label free. Additionally, they allow many reactions to be studied in real-time, allowing the reaction binding kinetics to be quantified in detail.

Surface plasmon polaritons (SPPs) (commonly called surface plasmons) are localized electromagnetic fields coupled to charge density oscillations at the interface of a metal and dielectric (see Raether H, *Surface Plasmons on Smooth and Rough Surfaces and on Gratings* (Springer, Berlin, 1988)). Surface plasmon resonance (SPR) sensors utilise the property that the surface plasmon polariton (SPP) is sensitive to changes in the local refractive index of the dielectric. The evanescent fields of the SPP decay into both the metal and dielectric media, with a decay length in the dielectric which is typically less than half the incident wavelength. For a planar interface the in-plane wavevector of the SPP, $k_{spp}$, is given by $$k_{spp} = k_0 \sqrt{\frac{\varepsilon_m \varepsilon_d}{\varepsilon_m + \varepsilon_d}} \qquad (1)$$

where $\varepsilon_m$ and $\varepsilon_d$ are the permittivities of the metal and dielectric media respectively and $k_0$ is the wave vector in free space. Any change in the local refractive index and therefore the permittivity ($\varepsilon_d$), either by way of a bulk index change, or, as for instance in the case of a biosensor, by the binding of an analyte to the SPP active interface thus changes the SPR excitation conditions. Various methods of probing these changes are utilised in SPR sensors such as angle (Matsubara K, Kawata S and Minami 1988 Optical chemical sensor based on surface plasmon measurement *Appl. Opt.* 27 1160-1163), wavelength (Zhang L M and Uttamchandani D 1988 Optical chemical sensing employing surface plasmon resonance *Electron. Lett.* 23 1469-1470) and phase (Nelson S G, Johnston K S and YEE S S1996 High sensitivity surface plasmon resonance sensor based on phase detection *Sens. Actuators B.* 35-36 187-191) intenogation, with varying degrees of sensitivity, and multiplexing capabilities, dependent upon the exact configuration, with the most sensitive methods allowing RI sensitivities of the order of $10^{-7}$ Refractive Index Units (RIU).

By controlling the surface chemistry at the SPP active interface a generic SPR sensing system can be tailored allowing a large range of different analytes to be monitored. Examples of detection studies found in the literature include: the monitoring of the pesticide atrazine in water, where real time analysis was undertaken by Minunni et al. and a detection limit of 0.05 ng mL$^{-1}$ was determined (Mininni M and Mascini M 1993 Detection of pesticide in drinking water using real-time biospecific interaction analysis (BIA). *Anal. Lett.* 26 1441-1460), the detection of concentrations of morphine as low as 0.1 ng mL$^{-1}$ obtained by Sakai et al. (Sakai G, Ogata K, Uda T, Miura N and Yamazoe 1998 N A surface plasmon resonance-based immunosensor for highly sensitive detection of morphine *Sens. Act. B.* 49 5-12), a concentration limit of 0.1 ng mL$^{-1}$ of methamphetamine using a SPR based biosensor developed by Sakai et al. (Sakai G, Nakata S, Uda T, Miura N and Yamazoe N 1999 Highly selective and sensitive SPR immunosensor for detection of methamphetamine *Electrochimica Acta.* 44 3849-3854), a lowest detection limit of 6 μg mL$^{-1}$ of *E. coli* by Spangler et al. (Spangler B D, Wilkinson E A, Murphy J T and Tyler B J 2001 Comparison of the spreeta surface plasmon resonance sensor and a quartz crystal microbalance for detection of *escherichia coli* heat-labile enterotoxin *Anal. Chimi. Acta.* 444 149-161) and Choi et al. used a commercial SPR sensor produced by Biacore (Biacore X) to detect botulinum toxin in concentrations as low as 2.5 μg mL$^{-1}$ (Kibong C, Wonjun S, Seunghee C and Jungdo Choi 1998 Evaluation of two types of biosensors for immunoassay of botulinum toxin *Biochem. Mol. Bio.* 31 101-105).

It is clear from this small sample of the literature that SPR sensors are regularly used in a wide range of fields including environmental analysis, medical diagnostics, food safety etc, as well as the previously mentioned drug discovery. However, their use is not limited to detection studies; they are also regularly used in research studies for subjects such as proteomics and surface chemistry. Examples include: Liu et al. used a SPP based sensor to measure the length of DNA with sub nanometre axial resolution (Gang L et al. A Nanoplasmonic Molecular ruler for measuring nuclease activity and DNA footprinting *Nat. nanotech.* 1 47-52 (2006)), Campagnolo et al. used protein marker detection of tumour-antigen and serum-antibody interactions, monitored in real time using a SPR sensor (Campagnolo C, Meyers K J, Ryan T, Stkindon R C, Chen Y T, Scanlan M L, Ritter G, Old L J and Batt C A 2004 Real-time, label-free monitoring of tumor antigen and serum antibody interactions J. *Biochem. Biophys. Methods.* 16 283-298), and Chou et al. developed a ferritin (a non-specific tumour marker) immunosensor using SPR sensing analysis (Chou S F, Hsu W L, Hwang J and Chen C Y 2004 Development of an immunosensor for human ferritin, a non-specific tumor marker, based on surface plasmon resonance *Biosens. Bioelectron.* 19 999-1005).

Polarisation of the incident light is discussed in I. R. Hooper, J. R. Sambles, "Sensing using differential surface plasmon ellipsometry", Journal of Applied Physics, Volume 96, Number 5 (September 2004), pp. 3004-3011; and in I. R. Hoooper, J. R. Sambles, "Differential ellipsometric surface plasmon resonance sensors with liquid crystal polarization modulators", Applied Physics Letters, Volume 85, Number 15 (October 2004), pp. 3017-3019.

SPR sensing techniques are constantly being developed and refined in order to meet the increasing performance demands required. As set out in Homola J 2003 Present and future of surface plasmon resonance biosensors *Anal. Bioanal. chem.* 377 528-539, there are 3 main avenues of research being focused upon, 1) increasing the sensitivity, 2) miniaturisation, so that SPR sensors can be utilised in the field and 3) increasing the number of simultaneous sensing channels.

Further background reading includes WO2008/007115, US2007/0216901, US2007/0159629, WO2007/061981, EP0341927 and Nylander et al "Gas Detection by means of surface plasmon resonance" T Sens Actuators, 3, 79-88 (1982).

STATEMENTS OF THE INVENTION

According to one aspect of the invention, there is provided a method of optimising the sensitivity of surface plasmon ellipsometry (SPE) apparatus used to analyse a surface comprising a conducting film, the method comprising calculating a sensitivity map of SPE for the film, the sensitivity map comprising data defining variations in sensitivity of said SPE apparatus with angle of incidence and polarisation angle of polarised light incident on said film for analysis by said SPE apparatus, and using said sensitivity map to configure said SPE apparatus with a combination of said angle of incidence and polarisation angle located in a region of substantially maximum sensitivity in said sensitivity map.

Said SPE apparatus typically comprises a light source; an input polariser set at an input polarisation angle to generate polarised light from said light source; a conducting film; an optical system having an internal angle wherein said polarised light is incident at an incident angle on said optical system to illuminate said conducting film with said polarised light to generate plasmons in said conducting film by total internal reflection of said polarised light; means for flowing fluid over said conducting film; and a detection system to detect an orientation of an elliptical polarisation of said totally internally reflected polarised light indicative of refractive index changes in said fluid. The optical system may comprise a prism, e.g. a 60° prism. The conducting film and optical system may be a Kretschmann-Raether arrangement.

The method may further comprise refining the angle of incidence by selecting an initial incident angle from the sensitivity map; conducting an angle scan over a small angle range, e.g. 5 to 10°, from said initial incident angle; said angle scan determining variation of the reflected polarised light with varying incident angle, and setting said angle of incidence to the value which provides the greatest variation in said reflected polarised light.

Said SPE apparatus may be configured with an (internal) angle of incidence slightly (for example 0.5-10% or 1-5%) lower than an SPR angle of an optical system of said SPE apparatus, e.g. 58° for an optical system having an internal angle of 60°. (Here the SPR angle may be defined as an angle of (peak) SPR resonance. In embodiments to obtain the highest sensitivity to changes in refractive index an incident angle on the low angle side of the SPR is used, preferably with an input polarisation in the range from 2° or 5° up to 20°, preferably of approximately 10° is used.

The conducting film may comprise gold. No two gold films will be identical, having slightly different thicknesses, surface roughness and consequentially permittivities. Thus each gold film will have its own sensitivity map. Analysing sensitivity maps for many different gold films shows that if the input polariser angle is set to approximately 15° and the angle of incidence is set to the optimum position, it is possible to be within approximately 10% of the highest possible sensitivity for a wide range of gold film parameters. Accordingly, the SPE apparatus may be configured to have a polarisation angle of 15°.

The SPE apparatus may further comprise a polarisation modulator, for example, a photo elastic modulator, to modulate a polarisation of said polarised light whereby the sensitivity of the apparatus is enhanced. The frequency of modulation may be 47 kHz. The method may comprise setting the orientation of the polarisation modulator relative to the input polarisation angle, i.e. at a 45° azimuthal angle relative to said input polarisation angle. The apparatus may further comprise a quarter wave plate and the method may further comprise setting the orientation of the quarter wave plate relative to the input polarisation angle, i.e. parallel to the polarisation angle. Since the orientation of both the polarisation modulator and the quarter wave plate are set relative to the input polarisation angle, the fact that they can remain at a fixed angle for different apparatus, e.g. different gold films, greatly simplifies the set-up procedure.

Polarised light reflected from said conducting film may have at least a first harmonic component and said sensitivity plotted in said sensitivity map may be defined as the differential of the amplitude of said first harmonic component with respect to changing permittivity of a fluid flowing over said conducting film. Said apparatus may further comprise an output polariser having an output polarisation angle and the method further comprises setting said output polarisation angle so that said amplitude of said first harmonic component is zero. This corresponds to the angle of the output polariser being at the minimum of the polarization ellipse and further optimizes the sensitivity of the SPE apparatus.

According to another aspect of the invention, there is provided a method of optimising plasmon resonance based sensing apparatus sensing refractive index changes in a fluid, the apparatus comprising a light source; an input polariser set at an input polarisation angle to generate polarised light from said light source; a sensor; an optical system having an internal angle wherein said polarised light is incident at an incident angle on said optical system to illuminate said sensor with said polarised light to generate plasmons in said sensor by total internal reflection of said polarised light; means for flowing said fluid over said sensor; and a detection system to detect an orientation of an elliptical polarisation of said totally internally reflected polarised light indicative of said refractive index changes in said fluid, the method comprising setting the input polariser to a predetermined input polarisation angle; selecting an initial incident angle; varying said incident angle over a small angle range from said initial incident angle; determining the variation of the reflected polarised light with varying incident angle, and setting said incident angle to the value which provides the greatest variation in said reflected polarised light.

The predetermined input polarisation angle is an input polarisation angle which when combined with an optimised angle of incidence results in an optimised or substantially optimised sensitivity, i.e. within 10% of the optimised sensitivity, of the apparatus. For example, for a gold conducting film, the predetermined input polarisation angle may be 15°.

The initial incident angle and/or predetermined input polarisation angle may be selected by calculating a sensitivity map plotting a measure of sensitivity against input polarisation angle and incident angle, determining the value of said input polarisation angle and said incident angle which together result in the greatest value of the measure of sensitivity. Said initial incident angle may be the incident angle resulting in the greatest value of the measure of sensitivity and said predetermined input polarisation angle may be the input polarisation angle which provides a value of sensitivity within 10% of the greatest sensitivity.

The apparatus may further comprise a polarisation modulator and/or a quarter wave plate and the method may further comprise setting the orientation of the polarisation modulator and quarter wave plate relative to the input polarisation angle.

According to another aspect of the invention, there is provided apparatus for reading a plasmon resonance sensor sensing refractive index changes in a fluid, the apparatus comprising: a light source; an input polariser set at a predetermined input polarisation angle to generate polarised light from said light source; a conducting film; an optical system having an internal angle wherein said polarised light is incident on said optical system at an incident angle to illuminate said sensor with said polarised light to generate plasmon in said conducting film by total internal reflection of said polarised light; means for flowing said fluid over said conducting film; and a detection system to detect an orientation of an elliptical polarisation of said totally internally reflected polarised light indicative of said refractive index changes in the fluid, wherein said apparatus is configured to have said incident angle and said input polarisation angle which optimise the sensitivity of the apparatus to said changes in refractive index.

The apparatus may thus be optimised as defined in the method above.

Said apparatus may further comprise a polarisation modulator to modulate a polarisation of said polarised light and said polarisation modulator may be set at a 45° or 90° azimuthal angle relative to said input polarisation angle. Said apparatus may further comprise a quarter wave plate and said quarter wave plate is set parallel to said input polarisation angle.

Said apparatus may further comprise an output polariser which is set at an output polarisation angle and which polarises the reflected polarised light before said reflected polarised light is incident on the detection system. Said output polarisation angle may be set at 45° from the azimuth of said reflected polarisation ellipse.

These techniques offer sensitivity levels comparable to the best SPR sensing methods. The sensors described may be simply multiplexed so as to produce an ultra-sensitive sensor with many parallel sensing channels.

FIGURES

Figure 4:
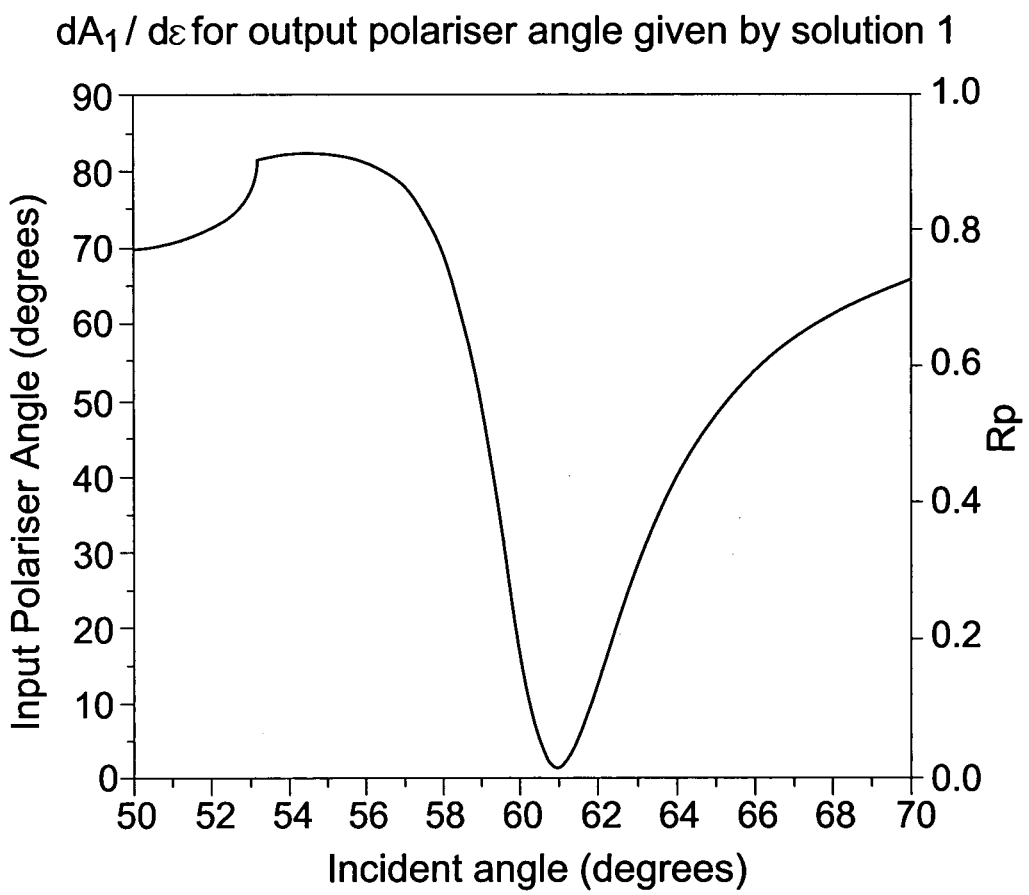
Figure 5:
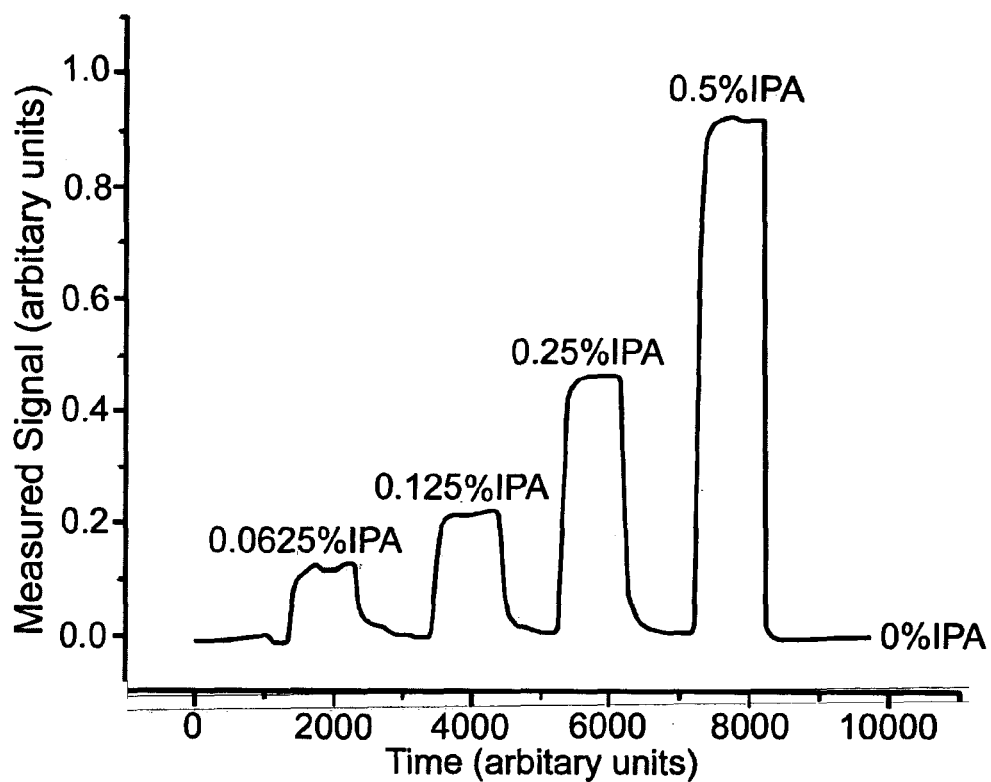
Figure 6:
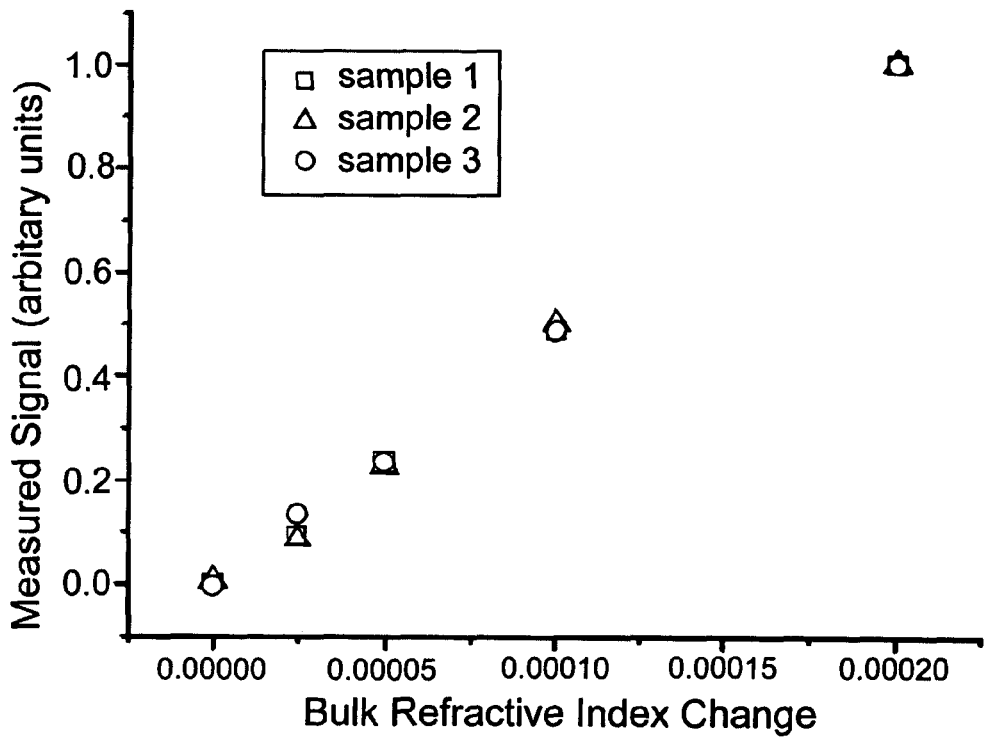

FIG. 4 is a sensitivity graph on which the modeled differential for $\omega_1$ is plotted as a function of the changing permittivity of dielectric in gray scale and the reflectivity for p polarized light is plotted as a line, and FIG. 5 is a graph showing the variation in measured signal as a function of time, and FIG. 6 is a graph showing the measuring signal as a function of the calculated refractive index for three fluid flow experiments.

Figure 1:
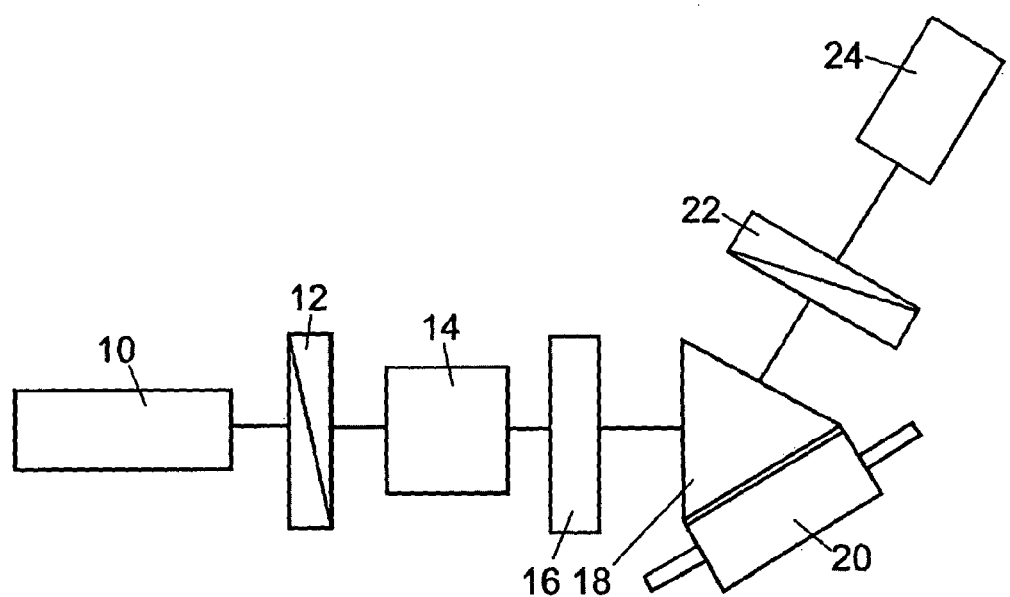
FIG. 1 is a schematic diagram of the apparatus used according to the invention.

FIG. 1 shows a plasmon resonance sensing system according to the invention. The system comprises a light source 10 in the form of a 632.8 nm wavelength HeNe laser and a first polarizer 12 positioned at a 15° azimuthal angle to polarize light from said light source. A sinusoidal modulation of the polarisation is added through the use of a combined Photo Elastic Modulator (PEM) 14 and quarter wave plate 16, with the frequency of modulation being approximately 47 kHz. The PEM 14 is placed after the first polariser at an azimuthal angle of 45° from the polariser angle. The quarter wave plate 16 is subsequently placed after the PEM at an angle parallel to the first polariser. The resultant polarisation state of the light exiting the quarter wave plate 16, is linear, with the plane of polarisation varying sinusoidally centred around the input polariser angle. (The polarisation state at any moment in time is always linear and this can be simply shown through use of Jones calculus).

The resulting modulated linearly polarised light is then incident through a 60° prism 18 on to a plasmon resonance sensor which is indexmatched to the prism in the Kretschmann-Raether arrangement (described in more detail in Kretschmann E and H Raether 1968 Surface plasmon resonance *Z Naturforsch. A.* 23A 2135). The sensor comprises an SF2 glass substrate (n=1.646 at 632.8 nm) coated with an ~50 nm thick gold film by thermal evaporation under ultra-high vacuum. A simple polytetrafluoroethylene (PTFE) flow cell 20 is affixed onto the gold coated surface. The flow cell providing a flow of a dielectric medium over the gold coated surface. The complete sensor and flow cell are mounted onto a computer controlled rotating table (with angular resolution of 0.001°). The modulated linearly polarised light is incident through the prism on to the gold film to generate plasmons as explained below. The reflected polarized light is detected by a detection system comprises a second polarizer 22 and a photodiode detector 24 connected to a lock-in amplifier monitoring at the modulation frequency.

A surface plasmon polariton (SPP) is a longitudinal surface charge density oscillation at the boundary between a metal and a dielectric. If the metal has a negative real part to $\in_m$ which is greater in magnitude than $\in_d$ then equation (1) shows that for a planar interface the incident radiation needs to have an in-plane wavevector enhanced beyond the maximum wavevector available in the dielectric. A simple way to achieve this is using attenuated total reflection in which radiation is incident within a prism at an angle beyond the critical angle for the surface which supports the SPP (see Raether H, *Surface Plasmons on Smooth and Rough Surfaces and on Gratings* (Springer, Berlin, 1988). Further in this planar geometry the SPP may only be coupled to by incident transverse magnetic (TM or p) polarised light as there must be a component of the incident E-field normal to the metal surface to excite the charge density oscillation.

Figure 2A:
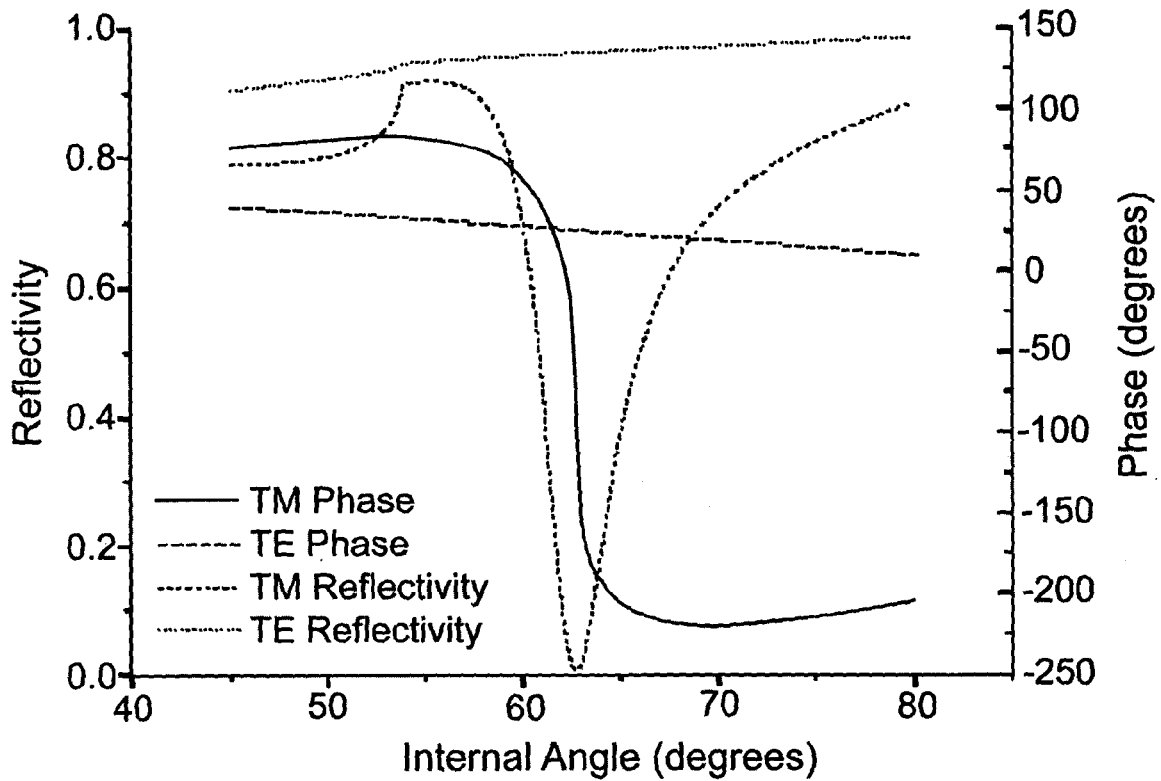
FIG. 2a is a graph on which the reflectivity and phase of both transverse magnetic (TM) light and transverse electric (TE) light is plotted as a function of the internal angle.

FIG. 2a shows that when linearly polarised light containing both TM and transverse electric (TE or s) components is incident upon a Kretschmann-Raether SPP system, near the SPR condition, there is a change in phase of the TM polarisation of the reflected light, whilst the phase of the TE polarised light is relatively unchanged. This effect is known and described, e.g. in Nylander C, Liedberg B and Lind T 1982 Gas detection by means of surface plasmon resonance *Sens. Actuators.* 3 79 (1982). In FIG. 2*a*, the reflectivity and phase of both TM and TE light is plotted as a function of the internal angle (i.e. the angle measured from the normal to an internal incident face for the light, in this example inside the prism) in a simple angle scanning system.

Figure 2B:
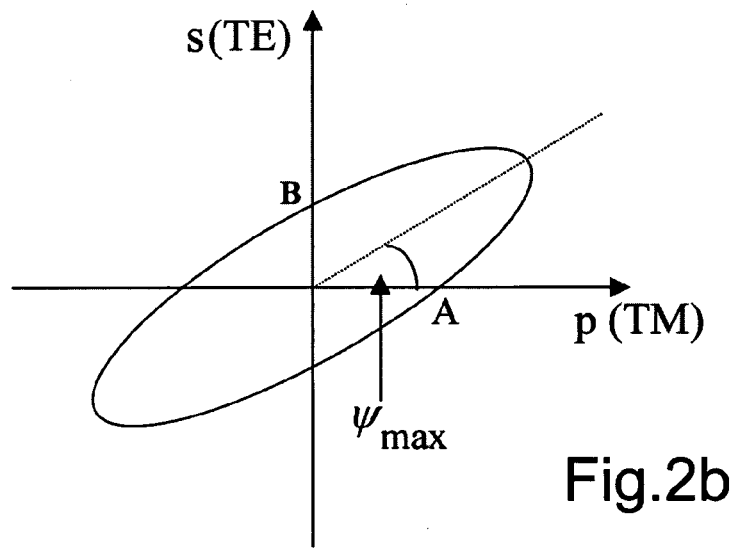
FIG. 2b is a schematic of the ellipse describing the light reflected from a Kretschmann SP system with incident light consisting of both s and p-components.

Because the two orthogonal polarisations (TM and TE) are phase shifted with respect to each other the reflected light becomes elliptically polarized as shown in FIG. 2*b* where $\psi_{max}$ is the azimuth of the ellipse, with A and B being the purely p and s components. Since the phase difference changes rapidly as a function of incident angle close to the resonance condition, the ellipticity and azimuth of the ellipse also change rapidly. An increase in the refractive index of the bounding dielectric moves the resonance and thereby changes the output optical phase. In particular, if an angle of incidence is chosen close to the resonance p-reflectivity minimum and the local refractive index of the bounding dielectric altered, the polarization state of the reflected light may change dramatically. Indeed, tiny changes of the refractive index can give macroscopic changes in the polarization state. For example, from multi-layer optics modelling it can be shown that a change in refractive index of $5 \times 10^{-5}$ RIU gives a 1° rotation of the azimuth of the polarisation when optimized (to be defined later) for a SPP excited on a gold film at a wavelength of 632.8 nm. Note that the corresponding change in ellipticity of the reflected light is much smaller than the change in the azimuth.

Given the relatively large change in polarisation state evident for small refractive index changes, a method of determining very small changes in the polarisation state will produce a refractive index sensor of exquisite sensitivity. Placing a polariser in the path of the reflected elliptically polarised light from a Kretschmann-Raether system and rotating the resultant transmission gives:

$$I = R_p \cos^2\phi \cos^2\psi + R_s \sin^2\phi \sin^2\psi + \frac{X}{2}\sin2\phi\sin2\psi \quad (2)$$

where $R_p = r_{pr}^2 + r_{pi}^2$, $R_s = r_{sr}^2 + r_{si}^2$ and $X = r_{pr}r_{sr} + r_{pi}r_{si}$, with $r_{[p,s][r,i]}$ corresponding to the real and imaginary components of the complex reflection amplitude coefficients for p- and s-polarised light, $\phi$ and $\chi$ being the input and output polariser angles respectively. A derivation of (2) can be found in Hooper I R and Sambles J R 2004 Sensing using differential surface plasmon ellipsometry *J. Appl. Phys.* 96 3004-3011. The rapid change in phase through the SPR is evident in corresponding rapid changes in the complex reflection amplitude coefficient for p-polarised light. Thus any change in the refractive index of the bounding dielectric produces a change in the transmitted intensity through the output polariser. Determining any change in the refractive index by monitoring changes in this intensity is most effective when the output polariser angle is set at 45° from the azimuth of the reflected polarisation ellipse. At this angle the largest change in transmitted intensity as a function of refractive index will be realised, with the change in transmitted intensity also being approximately linear with refractive index. The refractive index sensitivity of this method can be further improved upon through the use of a polarisation modulation technique.

As described above a sinusoidal modulation of the polarisation is added through the use of a combined Photo Elastic Modulator (PEM) and quarter wave plate. The light intensity transmitted through the output polariser is also periodically modulated. The intensity as a function of time can be modelled by substituting $\phi = \phi_0 + \Delta \sin(\omega t)$ into equation (2), where $\phi_0$ is the angle of the incident polariser, and $\Delta$ is the modulation amplitude. After expanding the resultant expression and collecting terms in $\omega$ the following relationships for the time invariant (DC), fundamental $A_1$ and first harmonic $A_2$ components are found $$DC = R_p\cos^2\phi_0\cos^2\psi + R_s\sin^2\phi_0\sin^2\psi + \frac{X}{2}\sin2\phi_0\sin2\psi \quad (3)$$

$$A_1 = \Delta[\sin2\phi_0(R_s\sin^2\psi - R_p\cos^2\psi) + X\sin2\psi\cos2\phi_0] \quad (4)$$

$$A_2 = \frac{\Delta^2}{2}[\cos\phi_0(R_s\sin^2\psi - R_p\cos^2\psi) - X\sin2\psi\sin2\phi_0] \quad (5)$$

It is to be noted that the expression for the fundamental harmonic component $A_1$ (eqn. (4)) is equal to the differential of eqn. (2) multiplied by the amplitude of modulation.

The reflected light signal is measured using a photodiode, with the amplitude ($A_1$) of the fundamental component of the signal being determined using a lock-in amplifier monitoring at the modulation frequency. To obtain the best refractive index sensitivity the $A_1$ signal is set to zero by changing the output polariser angle (this corresponds to the angle of the output polariser being at the minimum of the polarization ellipse). This is for a number of reasons; firstly the rate of change of the $A_1$ signal around the zero point is at a maximum, secondly this change of signal is linear with changing refractive index and, finally, the $A_1$ signal is independent of intensity and therefore fluctuations in the laser intensity have little effect on the monitored signal.

Thus far the influence of only certain parameters upon the refractive index sensitivity has been considered. Determining the ideal incident polariser angle (proportion of p- and s-polarised components), and incident angle in the Kretschmann-Raether configuration, has not been discussed. It has already been mentioned that it is desirable to operate around the $A_1=0$ position. In this case eqn. 4 can be set to zero and solved for the output polariser angle, for which there are 2 possible solutions:

$$\psi_{1,2} = \pm\cos^{-1}\left[\sqrt{\frac{(R_p^2 + R_pR_s + 2X^2 - (R_p^2 + R_pR_s - 2X^2)\cos4\phi_0 \pm 2\sqrt{2}X\cos2\phi_0\sqrt{R_pR_s + X^2 + (X^2 - R_pR_s)\cos4\phi_0}}{(R_p + R_s)^2 + 4X^2 - ((R_p + R_s)^2 - 4X^2)\cos4\phi_0}}\right] \quad (5)$$

With $\psi_1$ corresponding to the positive solution, and $\psi_2$ the negative solution. For X<0, $\psi_1$ is the angle of the output polariser corresponding to the minimum of the polarization ellipse, whilst $\psi_2$ is the solution for the maximum of the polarisation ellipse. However when X>0 the reverse is true. In the case where X=0, which can occur for specific combinations of parameters, $\psi_1=-\psi_2$ and the DC level is symmetric with $\psi$. Therefore, under this condition the two solutions for the DC component are equal and the light is circularly polarised.

Figure 3:
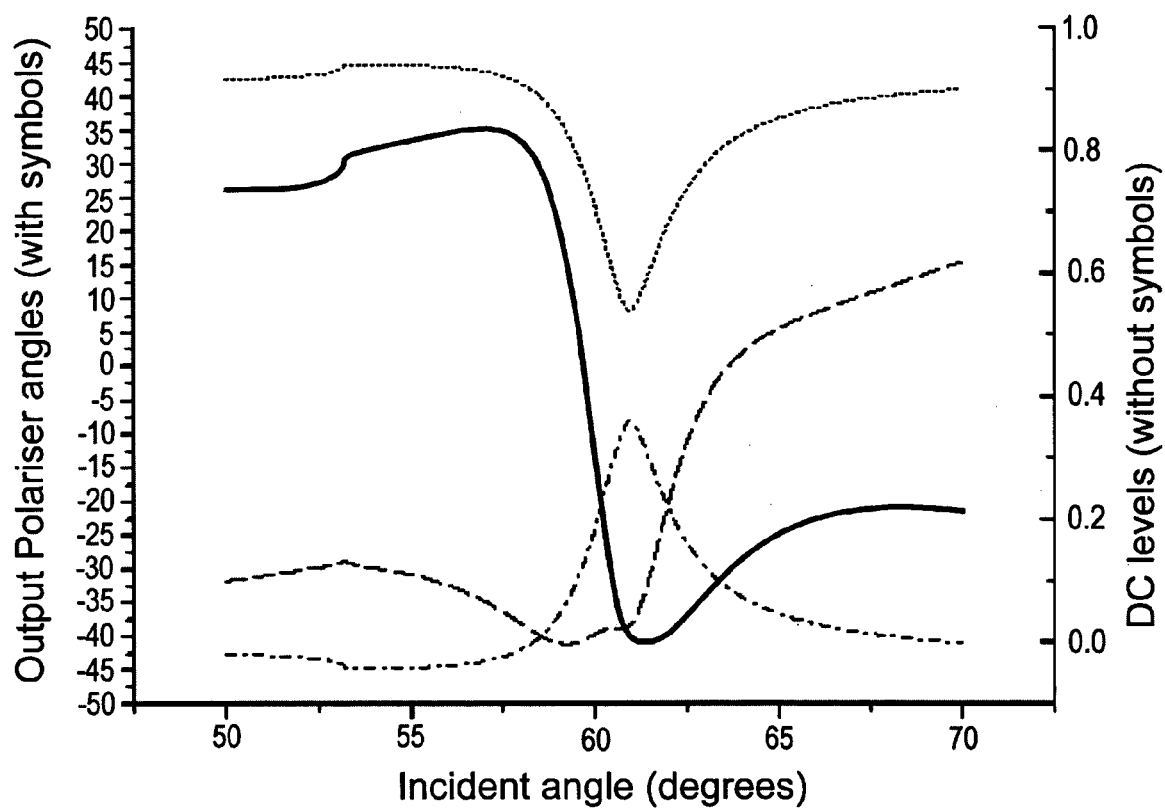
FIG. 3 is a graph on which two output polarizer angles and resultant DC levels are plotted as a function of incident angle.

FIG. 3 plots the changing roles of $\psi_1$ and $\psi_2$ where the two solutions for the output polariser angle which give $A_1=0$ are plotted as a function of changing incident angle with $\psi_1$ plotted as a continuous line and with $\psi_2$ plotted as a dashed line. Also plotted on the same graph are the corresponding DC levels for each solution (the dotted line being associated with the solution for $\psi_1$ and the dot-dash line being associated with the solution for $\psi_2$). At the crossing point of the two solutions for the output polarizer angles, the magnitudes of the DC levels are equal and the light is circularly polarized. This would give effectively no sensitivity to changes of refractive index. In this case the "crossed" and "parallel" polarisers are undefined. For the avoidance of doubt, it is noted that the input polarizer angle is set at 45° for the results shown in FIG. 3.

The highest sensitivity will occur when the rate of change of the $A_1$ signal with changing refractive index in the adjacent dielectric medium is at its largest. A change in refractive index produces a change in the complex reflection amplitude coefficients. Here, the derivatives of the reflection amplitude coefficients with respect to the permitivitty of the bounding dielectric were obtained by use of a multilayer optics code based upon recursive Fresnel equations (Reitz J R, Milford F J, Christy R W *Foundations of electromagnetic theory* (Addison-Wesley, Reading (MA), 1992)). The differentials of $A_1$ with respect to the amplitude coefficients are obtained analytically from eqn. (4) and are:

$$\frac{dA_1}{dr_{pr}} = \Delta(-2\sin 2\phi_0 r_{pr} \cos^2\psi + \sin 2\psi \cos 2\phi_0 r_{sr}) \quad (6)$$

$$\frac{dA}{dr_{sr}} = \Delta(2\sin 2\phi_0 r_{sr} \sin^2\psi + \sin 2\psi \cos 2\phi_0 r_{pr}) \quad (7)$$

$$\frac{dA_1}{dr_{pi}} = \Delta(-2\sin 2\phi_0 r_{pi} \cos^2\psi + \sin 2\psi \cos 2\phi_0 r_{si}) \quad (8)$$

$$\frac{dA_1}{dr_{si}} = \Delta(2\sin 2\phi_0 r_{si} \sin^2\psi + \sin 2\psi \cos 2\phi_0 r_{pi}) \quad (9)$$

where $\psi$ is given by eqn (5).

Combining eqns 6, 7, 8, and 9 with the numerically calculated values for $$\frac{dr_{[p,s][r,i]}}{d\varepsilon}$$

and using, $$\frac{dA_1}{d\varepsilon} = \frac{dA_1}{dr_{pr}} \cdot \frac{dr_{pr}}{d\varepsilon} + \frac{dA_1}{dr_{sr}} \cdot \frac{dr_{sr}}{d\varepsilon} + \frac{dA_1}{dr_{pi}} \cdot \frac{dr_{pi}}{d\varepsilon} + \frac{dA_1}{dr_{si}} \cdot \frac{dr_{si}}{d\varepsilon} \quad (10)$$

allows the calculation of sensitivity maps, from which the input polarisation angle and incident angle in the Kretschmann-Raether configuration giving the highest sensitivity to refractive index changes can be obtained.

In FIG. 4, an example of such a modeled sensitivity map for a 50 nm thick gold film with a permittivity of $\in_m = -10+i$ for an incident wavelength of 632.8 mu is shown. Plotted as a grey scale is the differential of $A_1$ with respect to the permittivity of the dielectric $\in_d$ (for the solution using $\psi_1$) as a function of incident angle (measured from the normal to the input face of the prism) and input polariser angle (with the angle giving TM polarised light being defined as 0°). The areas of dark and light correspond to the larger gradients, with a mid-grey being zero. For clarity the reflectivity of TM polarised light is also plotted as a line graph.

It is clear from this plot that to obtain the highest sensitivity to changes in refractive index, i.e. to obtain the greatest gradient, an incident angle slightly below the SPR incident angle with an input polarisation of approximately 10° to is required 15°. Thus to obtain the highest sensitivity to changes in refractive index an incident angle on the low angle side of the SPR with an input polarisation of approximately 10° is used.

No two gold films produced will be identical, having slightly different thicknesses, surface roughness and consequentially permittivities. This in turn affects the SPR excitation conditions. Thus each gold film produced will have its own sensitivity map and requires its own optimum setup. By analysing modelled sensitivity maps for many different films it becomes clear that if the input polariser is set to ~15°, with the incident angle set to the optimum position, it is possible to be within ~10% of the highest possible sensitivity for a wide range of gold film parameters (comfortably within the range of easy reproducibility). Since the orientations of both the PEM and quarter wave plate are set relative to the input polariser angle the fact that they can remain at a fixed angle for different gold films greatly simplifies the set-up procedure, with the only remaining setup parameter being the incident angle in the Kretschmann-Raether configuration, which is readily set empirically.

To obtain the highest possible refractive index sensitivity the optimal angle of incidence needs to be determined. As set out above, this angle occurs on the lower angle side of the SPR. Using the fact that, for small refractive index and incident angle changes, a change in incident angle at a fixed refractive index is equivalent to a change in refractive index at fixed incident angle, it is possible to use angle scans to determine this optimal angle. An incident angle is chosen and the output polariser is rotated to ensure that the signal measured on the lock-in amplifier (the fundamental frequency component) is as close to zero as possible (i.e. the output polariser is oriented at the minimum of the reflected polarisation ellipse). An incident angle scan is then performed over a small angle range (a few degrees), with the gradient of the signal as a function of the incident angle being determined. This is performed for several initial incident angles, with the angle at which the largest gradient is obtained (often interpolated from the points measured) being chosen. This gives a maximum change in signal as a consequence of shifts in the SPR condition.

To measure the absolute sensitivity of the system to changes in refractive index different liquids of known refractive index are passed through the flow-cell and the change in signal monitored. This was achieved by use of solutions consisting of dilutions of isopropan-2-ol (IPA) in water. The solutions used here were 0.5%, 0.25%, 0.125% and 0.0625% IPA by volume in water, created by binary division of a 1% solution. At these low percentages the change in refractive index as a function of concentration is linear, and therefore the refractive index of each solution is readily calculated. (At room temperature the refractive index of water is 1.33 at 632.8 nm whilst that of IPA is 1.37.)

Pure water was flowed through the cell at 4.95 ml h$^4$ using a syringe pump. After the baseline level had been established the water was replaced with an IPA in water solution before reverting back to pure water again. This process was then performed for all other TA-in-water solutions, with the results for one typical series of experiments shown in FIG. 5. Plotted is the measured signal as a function of time (with time units approximately seconds), with each step change corresponding to a bulk refractive index change. Noticeable in the plot are small variations in the signal immediately preceding each bulk index change. These are caused by sudden changes in the pressure of the fluid, leading to a small change in the refractive index, when the solutions are exchanged in the syringe pump. A slowly varying trend in the data linked to temperature drift of the sample has been removed.

One method for determining the sensitivity of the system, or smallest resolvable index change, is to divide the signal difference obtained when the fluid in the system is changed by twice the standard deviation of the noise (If Gaussian noise is assumed, 95% of the data points will lie within 2 standard deviations of the mean value of the signal), and then multiplying this by the index change corresponding to that change of fluid. Several experiments were performed similar to that resulting in FIG. 5. The results of all these three experiments are tabulated below along with their associated errors. It is clear from these results that repeatable refractive index sensitivities of better than $5 \times 10^{-7}$ RIU are obtained.

| Sample | Sensitivity [RIU] | Associated Error [RIU] |
|---|---|---|
| 1 | 3.0E−07 | ±4.4E−08 |
| 2 | 3.5E−07 | ±6.4E−08 |
| 3 | 3.5E−07 | ±1.9E−08 |

Another important feature of a bio-chemical sensor is linearity. Here the test of linearity is shown in FIG. 6, where the measured signal as a function of the expected refractive index change for 3 typical experiments is presented. The variations in the three data sets are believed to be not due to errors in the measurement of the refractive index, but rather to small variations in the mixing process used to produce the IPA in water solutions. This data shows that the method is linear over a range of refractive index changes of up to at least $2 \times 10^{-4}$ RIU, though it is expected that the linear range will be much greater than this.

Like most of the current SPR based sensors in use (see e.g. Homola J 2003 Present and future of surface plasmon resonance biosensors *Anal. Bioanal. chem.* 377 528-539); the described arrangement will suffer from variations in refractive index associated with environmental factors, in particular variations in temperature and pressure. Achieving higher sensitivities requires very good control of these variables, or the use of reference channels to eliminate their effects. Thus one of the driving forces behind multi-channel sensors is to not only detect multiple analytes simultaneously, but also to allow such reference channels. By use of phase sensitive array detectors (see Pitter M C, Goh J Y L, Somekh M G, Hayes-Gill B R, Clark M and MorganS P 2003 Phase-sensitive CMOS photo-circuit array for modulated thermoreflectance measurements *Electron. Lett.* 39 1339-1340) differential imaging using differential ellipsometry of waveguide modes can be achieved (see Hooper I R, Sambles J R, Pitter M C and Somekh M G 2006 Phase sensitive array detection with polarisation modulated differential sensing *Sens. Act. B.* 119 651-655) and work is ongoing to produce a similar imaging system for an arrayed SPR sensor.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. The method of optimising the sensitivity of surface plasmon ellipsometry (SPE) apparatus used to analyse a surface comprising a conducting film, the method comprising calculating a sensitivity map of SPE for the film, the sensitivity map comprising data defining variations in sensitivity of said SPE apparatus with angle of incidence and polarisation angle of polarised light incident on said film for analysis by said SPE apparatus, and using said sensitivity map to configure said SPE apparatus with a combination of said angle of incidence and polarisation angle located in a region of substantially maximum sensitivity in said sensitivity map.

2. The method according to claim 1, comprising further optimising the angle of incidence by selecting an initial incident angle from the sensitivity map; performing an angle scan over a small angle range from said initial incident angle; said angle scan defining variation of polarised light reflected from said conducting film with varying incident angle, and configuring said SPE apparatus with said angle of incidence which provides the greatest variation in said reflected polarised light.

3. The method according to claim 1, comprising configuring said SPE apparatus with an angle of incidence slightly lower than an SPR angle of an optical system of said SPE apparatus.

4. The method according to claim 1, wherein the conducting film comprises gold film.

5. The method according to claim 4, comprising selecting a polarisation angle of 15°.

6. The method according to claim 1, comprising defining sensitivity as the differential of the amplitude of a first harmonic component of polarised light reflected from said conducting film with respect to changing permittivity of a fluid flowing over said conducting film.

7. The method according to claim 6, wherein the apparatus further comprises an output polariser having an output polarisation angle and the method further comprises setting said output polarisation angle so that said amplitude of said first harmonic component is zero.

8. Surface plasmon ellipsometry (SPE) apparatus for sensing refractive index changes in a fluid, the apparatus comprising
a light source;
an input polariser having an input polarisation angle to generate polarised light from said light source;
a conducting film;
an optical system having an internal angle wherein said polarised light is incident on said optical system at an incident angle to illuminate said conducting film with said polarised light to generate plasmons in said conducting film by total internal reflection of said polarised light;
means for flowing said fluid over said system; and
a detection system to detect an orientation of an elliptical polarisation of said totally internally reflected polarised light indicative of said refractive index changes in said fluid
wherein sensitivity of said apparatus is optimised according to the method of claim 1.

9. The apparatus according to claim 8, comprising a polarisation modulator to modulate a polarisation of said polarised light.

10. The apparatus according to claim 9, wherein said polarisation modulator is set at a 45° azimuthal angle relative to said input polarisation angle.

11. The apparatus according to claim 9, comprising a quarter wave plate.

12. The apparatus according to claim 11, wherein said quarter wave plate is set parallel to said input polarisation angle.

* * * * *